(12) United States Patent
Prior et al.

(10) Patent No.: US 10,792,057 B2
(45) Date of Patent: Oct. 6, 2020

(54) ARTICULATION MECHANISMS FOR TISSUE SPECIMEN RETRIEVAL DEVICES AND TISSUE SPECIMEN RETRIEVAL DEVICES INCORPORATING THE SAME

(71) Applicant: COVIDIEN LP, Mansfield, MA (US)

(72) Inventors: Scott J. Prior, Shelton, CT (US); Nikolai D. Begg, Wayland, MA (US)

(73) Assignee: Covidien LP, Mansfield, MA (US)

( * ) Notice: Subject to any disclaimer, the term of this patent is extended or adjusted under 35 U.S.C. 154(b) by 139 days.

(21) Appl. No.: 15/933,825

(22) Filed: Mar. 23, 2018

(65) Prior Publication Data
US 2019/0290301 A1    Sep. 26, 2019

(51) Int. Cl.
*A61B 17/221*     (2006.01)
*A61B 17/00*      (2006.01)
(Continued)

(52) U.S. Cl.
CPC ...... *A61B 17/221* (2013.01); *A61B 17/00234* (2013.01); *A61B 2017/00287* (2013.01);
(Continued)

(58) Field of Classification Search
CPC ........ A61B 17/221; A61B 2017/00287; A61B 2017/00336; A61B 2017/22034; A61B 2017/2212; A61B 2017/32056
(Continued)

(56) References Cited

U.S. PATENT DOCUMENTS 5,441,499 A   8/1995 Fritsch
5,643,283 A   7/1997 Younker
(Continued)

FOREIGN PATENT DOCUMENTS

DE   202015008447 U1   3/2016
EP       0557963 A1   9/1993
(Continued)

OTHER PUBLICATIONS

Extended European Search Report issued in corresponding European Application No. 19164532.4 dated Aug. 8, 2019, 11 pages.

*Primary Examiner* — Gregory A Anderson
*Assistant Examiner* — Alyssa M Keane
(74) *Attorney, Agent, or Firm* — Carter, DeLuca & Farrell, LLP (57) ABSTRACT

A tissue specimen retrieval device includes a housing, an outer shaft extending from the housing, an end effector assembly extending from the outer shaft, an actuator associated with the housing, and an articulation mechanism operably coupled between the actuator and the end effector assembly. The articulation mechanism includes an articulation block supporting the end effector assembly thereon and is rotatable between first and second orientations to articulate the end effector assembly. A spring biases the articulation block towards the second orientation. An actuation sleeve is slidable relative to the articulation block, in response to actuation of the actuator, from an engaged position, wherein the actuation sleeve is disposed about and retains the articulation block in the first orientation, to a disengaged position, wherein the actuation sleeve is spaced from the articulation block such that the articulation block rotates to the second orientation to articulate the end effector assembly.

10 Claims, 7 Drawing Sheets

(51) Int. Cl.
*A61B 17/22* (2006.01)
*A61B 17/29* (2006.01)

(52) U.S. Cl.
CPC ........... *A61B 2017/00336* (2013.01); *A61B 2017/22034* (2013.01); *A61B 2017/2927* (2013.01)

(58) Field of Classification Search
USPC ........................................ 606/113, 114, 127
See application file for complete search history.

(56) References Cited

U.S. PATENT DOCUMENTS

| | | | |
|---|---|---|---|
| 6,059,793 A | 5/2000 | Pagedas | |
| 6,156,055 A | 12/2000 | Ravenscroft | |
| 6,162,209 A | 12/2000 | Gobron et al. | |
| 6,171,317 B1 | 1/2001 | Jackson et al. | |
| 6,206,889 B1 | 3/2001 | Bennardo | |
| 6,224,612 B1 | 5/2001 | Bates et al. | |
| 6,228,095 B1 | 5/2001 | Dennis | |
| 6,248,113 B1 | 6/2001 | Fina | |
| 6,258,102 B1 | 7/2001 | Pagedas | |
| 6,264,663 B1 | 7/2001 | Cano | |
| 6,270,505 B1 | 8/2001 | Yoshida et al. | |
| 6,280,451 B1 | 8/2001 | Bates et al. | |
| 6,344,026 B1 | 2/2002 | Burbank et al. | |
| 6,350,266 B1 | 2/2002 | White et al. | |
| 6,350,267 B1 | 2/2002 | Stefanchik | |
| 6,358,198 B1 | 3/2002 | Levin et al. | |
| 6,368,328 B1 | 4/2002 | Chu et al. | |
| 6,383,195 B1 | 5/2002 | Richard | |
| 6,383,197 B1 | 5/2002 | Conlon et al. | |
| 6,387,102 B2 | 5/2002 | Pagedas | |
| 6,406,440 B1 | 6/2002 | Stefanchik | |
| 6,409,733 B1 | 6/2002 | Conlon et al. | |
| 6,447,523 B1 | 9/2002 | Middleman et al. | |
| 6,530,923 B1 | 3/2003 | Dubrul et al. | |
| 6,537,273 B1 | 3/2003 | Sosiak et al. | |
| 6,752,822 B2 | 6/2004 | Jespersen | |
| 6,805,699 B2 | 10/2004 | Shimm | |
| 6,951,533 B2 | 10/2005 | Foley | |
| 6,986,774 B2 | 1/2006 | Middleman et al. | |
| 7,037,275 B1 | 5/2006 | Marshall et al. | |
| 7,052,501 B2 | 5/2006 | McGuckin, Jr. | |
| 7,087,062 B2 | 8/2006 | Dhindsa | |
| 7,101,379 B2 | 9/2006 | Gregory, Jr. et al. | |
| 7,101,380 B2 | 9/2006 | Khachin et al. | |
| 7,112,172 B2 | 9/2006 | Orban et al. | |
| 7,115,125 B2 | 10/2006 | Nakao et al. | |
| 7,144,400 B2 | 12/2006 | Byrum et al. | |
| 7,169,154 B1 | 1/2007 | Due et al. | |
| 7,229,418 B2 | 6/2007 | Burbank et al. | |
| 7,285,126 B2 | 10/2007 | Sepetka et al. | |
| 7,316,692 B2 | 1/2008 | Huffmaster | |
| 7,357,801 B2 | 4/2008 | Burbank et al. | |
| 7,534,252 B2 | 5/2009 | Sepetka et al. | |
| 7,547,310 B2 | 6/2009 | Whitfield | |
| 7,615,013 B2 | 11/2009 | Clifford et al. | |
| 7,618,437 B2 | 11/2009 | Nakao | |
| 7,645,283 B2 | 1/2010 | Reynolds et al. | |
| 7,670,346 B2 | 3/2010 | Whitfield | |
| 7,678,118 B2 | 3/2010 | Bates et al. | |
| 7,722,626 B2 | 5/2010 | Middleman et al. | |
| 7,727,227 B2 | 6/2010 | Teague et al. | |
| 7,731,722 B2 | 6/2010 | Lavelle et al. | |
| 7,731,723 B2 | 6/2010 | Kear et al. | |
| 7,762,959 B2 | 7/2010 | Bilsbury | |
| 7,762,960 B2 | 7/2010 | Timberlake et al. | |
| 7,875,038 B2 | 1/2011 | Due et al. | |
| 7,892,242 B2 | 2/2011 | Goldstein | |
| 7,914,540 B2 | 3/2011 | Schwartz et al. | |
| 7,918,860 B2 | 4/2011 | Leslie et al. | |
| 7,955,292 B2 | 6/2011 | Leroy et al. | |
| 8,057,485 B2 | 11/2011 | Hollis et al. | |
| 8,075,567 B2 | 12/2011 | Taylor et al. | |
| 8,118,816 B2 | 2/2012 | Teague | |
| 8,152,820 B2 | 4/2012 | Mohamed et al. | |
| 8,172,772 B2 | 5/2012 | Zwolinski et al. | |
| 8,211,115 B2 | 7/2012 | Cheng et al. | |
| 8,282,572 B2 | 10/2012 | Bilsbury | |
| 8,337,510 B2 | 12/2012 | Rieber et al. | |
| 8,348,827 B2 | 1/2013 | Zwolinski | |
| 8,409,216 B2 | 4/2013 | Parihar et al. | |
| 8,414,596 B2 | 4/2013 | Parihar et al. | |
| 8,419,749 B2 | 4/2013 | Shelton, IV et al. | |
| 8,425,533 B2 | 4/2013 | Parihar et al. | |
| 8,430,826 B2 | 4/2013 | Uznanski et al. | |
| 8,435,237 B2 | 5/2013 | Bahney | |
| 8,444,655 B2 | 5/2013 | Parihar et al. | |
| 8,486,087 B2 | 7/2013 | Fleming | |
| 8,512,351 B2 | 8/2013 | Teague | |
| 8,579,914 B2 | 11/2013 | Menn et al. | |
| 8,585,712 B2 | 11/2013 | Cyprey et al. | |
| 8,591,521 B2 | 11/2013 | Cherry et al. | |
| 8,652,147 B2 | 2/2014 | Hart | |
| 8,721,658 B2 | 5/2014 | Kahle et al. | |
| 8,734,464 B2 | 5/2014 | Grover et al. | |
| 8,777,961 B2 | 7/2014 | Cabrera et al. | |
| 8,795,291 B2 | 8/2014 | Davis et al. | |
| 8,821,377 B2 | 9/2014 | Collins | |
| 8,827,968 B2 | 9/2014 | Taylor et al. | |
| 8,870,894 B2 | 10/2014 | Taylor et al. | |
| 8,906,035 B2 | 12/2014 | Zwolinski et al. | |
| 8,956,370 B2 | 2/2015 | Taylor et al. | |
| 8,968,329 B2 | 3/2015 | Cabrera | |
| 8,986,321 B2 | 3/2015 | Parihar et al. | |
| 9,005,215 B2 | 4/2015 | Grover et al. | |
| 9,017,328 B2 | 4/2015 | Bahney | |
| 9,017,340 B2 | 4/2015 | Davis | |
| 9,033,995 B2 | 5/2015 | Taylor et al. | |
| 9,084,588 B2 | 7/2015 | Farascioni | |
| 9,101,342 B2 | 8/2015 | Saleh | |
| 9,113,848 B2 | 8/2015 | Fleming et al. | |
| 9,113,849 B2 | 8/2015 | Davis | |
| 9,308,008 B2 | 4/2016 | Duncan et al. | |
| 9,364,201 B2 | 6/2016 | Orban, III | |
| 9,364,202 B2 | 6/2016 | Menn et al. | |
| 9,370,341 B2 | 6/2016 | Ceniccola et al. | |
| 9,370,378 B2 | 6/2016 | O'Prey et al. | |
| 9,375,224 B2 | 6/2016 | Jansen | |
| 9,414,817 B2 | 8/2016 | Taylor et al. | |
| 9,468,452 B2 | 10/2016 | Menn et al. | |
| 9,486,188 B2 | 11/2016 | Secrest et al. | |
| 9,522,034 B2 | 12/2016 | Johnson et al. | |
| 9,549,747 B2 | 1/2017 | Carlson | |
| 9,579,115 B2 | 2/2017 | Kahle et al. | |
| 9,592,067 B2 | 3/2017 | Hartoumbekis | |
| 9,622,730 B2 | 4/2017 | Farascioni | |
| 9,629,618 B2 | 4/2017 | Davis et al. | |
| 9,642,638 B1 | 5/2017 | Carrier | |
| 9,655,644 B2 | 5/2017 | Collins | |
| 9,730,716 B2 | 8/2017 | Secrest et al. | |
| 9,789,268 B2 | 10/2017 | Hart et al. | |
| 9,808,228 B2 | 11/2017 | Kondrup et al. | |
| 9,826,997 B2 | 11/2017 | Cherry et al. | |
| 9,867,600 B2 | 1/2018 | Parihar et al. | |
| 9,877,893 B2 | 1/2018 | Taylor et al. | |
| 2003/0144672 A1 | 7/2003 | Gellman et al. | |
| 2007/0088370 A1* | 4/2007 | Kahle | A61B 17/00234 606/114 |
| 2011/0087235 A1* | 4/2011 | Taylor | A61B 17/00234 606/114 |
| 2016/0256145 A1 | 9/2016 | Ceniccola et al. | |

FOREIGN PATENT DOCUMENTS

| | | |
|---|---|---|
| EP | 2583629 A2 | 4/2013 |
| WO | 9509666 A1 | 4/1995 |
| WO | 2004002334 A1 | 1/2004 |
| WO | 2014158880 A1 | 10/2014 |

* cited by examiner

Fig. 7 ns for
tissue specimen retrieval devices and tissue specimen retrieval devices incorporating the same to facilitate retrieval of a tissue specimen from the internal body cavity.

ARTICULATION MECHANISMS FOR TISSUE SPECIMEN RETRIEVAL DEVICES AND TISSUE SPECIMEN RETRIEVAL DEVICES INCORPORATING THE SAME

BACKGROUND

Technical Field

The present disclosure relates to tissue specimen retrieval from an internal body cavity and, more particularly, to articulation mechanisms for tissue specimen retrieval devices and tissue specimen retrieval devices incorporating the same to facilitate retrieval of a tissue specimen from the internal body cavity.

Background of Related Art

In minimally-invasive surgical procedures, operations are carried out within an internal body cavity through small entrance openings in the body. The entrance openings may be natural passageways of the body or may be surgically created, for example, by making a small incision into which a cannula is inserted.

Minimally-invasive surgical procedures may be used for partial or total retrieval of a tissue specimen from an internal body cavity. However, the restricted access provided by minimally-invasive openings (natural passageways and/or surgically created openings) presents challenges with respect to maneuverability and visualization. The restricted access also presents challenges when the tissue specimen is required to be removed. As such, a tissue specimen that is deemed too large for intact retrieval may be broken down into a plurality of smaller pieces to facilitate retrieval from the internal body cavity.

During such minimally-invasive surgical procedures, it is common that a cyst, tumor, or other affected tissue specimen is required to be removed. In these and other procedures where cancerous tissue is required to be removed, retrieval of the tissue specimen in an enclosed environment is highly desirable to inhibit seeding of cancer cells. Thus, with respect to breaking down large tissue specimens for retrieval through minimally-invasive openings, there is the added challenge of doing so within an enclosed environment.

SUMMARY

The present disclosure provides articulation mechanisms for tissue specimen retrieval devices and tissue specimen retrieval devices incorporating the same to facilitate retrieval of the tissue specimen from the internal body cavity. These and other aspects and features of the present disclosure are detailed below. As used herein, the term "distal" refers to the portion that is described which is further from a user, while the term "proximal" refers to the portion that is being described which is closer to a user. Further, any or all of the aspects and features described herein, to the extent consistent, may be used in conjunction with any or all of the other aspects and features described herein.

Provided in accordance with aspects of the present disclosure is a tissue specimen retrieval device including a housing, an outer shaft extending distally from the housing and defining a longitudinal axis, an end effector assembly extending distally from the outer shaft in a deployed position of the end effector assembly, an actuator operably associated with the housing, and an articulation mechanism operably coupled between the actuator and the end effector assembly. The articulation mechanism includes an articulation block supporting the end effector assembly thereon and rotatable between a first orientation and a second orientation to thereby articulate the end effector assembly between an aligned position and an articulated position. The articulation mechanism further includes a spring operably associated with the articulation block and configured to bias the articulation block towards the second orientation, and an actuation sleeve slidable relative to the articulation block, in response to actuation of the actuator, from an engaged position, wherein the actuation sleeve is disposed about the articulation block to thereby retain the articulation block in the first orientation, to a disengaged position, wherein the actuation sleeve is positioned proximally of the articulation block such that the articulation block rotates to the second orientation under the bias of the spring to thereby articulate the end effector assembly from the aligned position to the articulated position.

In an aspect of the present disclosure, in the first orientation, the articulation block defines a first operable dimension less than a diameter of the actuation sleeve to permit receipt of the articulation block within the actuation sleeve and, in the second orientation, the articulation block defines a second operable dimension greater than the diameter of the actuation sleeve to inhibit return of the articulation block into the actuation sleeve.

In another aspect of the present disclosure, the actuation sleeve is further movable from the disengaged position to a locked position, wherein the actuation sleeve is moved to abut the second operable dimension of the articulation block, thereby locking the end effector assembly in the articulated position or a further articulated position.

In still another aspect of the present disclosure, the articulation block is pivotable about a pivot pin. In such aspects, the spring may be a torsion spring disposed about the pivot pin.

In yet another aspect of the present disclosure, the end effector assembly includes first and second arms configured to support a tissue specimen bag thereon.

In still yet another aspect of the present disclosure, the end effector assembly is deployable relative to the outer shaft from a retracted position, wherein the end effector assembly is disposed within the outer shaft, to the deployed position. Another actuator may be provided and operably associated with the housing to selectively deploy the end effector assembly from the retracted position to the extended position.

Another tissue specimen retrieval device provided in accordance with aspects of the present disclosure includes a housing, an outer shaft extending distally from the housing and defining a longitudinal axis, an end effector assembly movable relative to the outer shaft, an actuator operably associated with the housing, an inner shaft operably coupled to the actuator at a proximal end portion of the inner shaft and extending distally from the actuator through the housing and the outer shaft, and an articulation mechanism operably coupled between the inner shaft and the end effector assembly. The articulation mechanism includes an articulation block pivotably supported at a distal end portion of the inner shaft, supporting the end effector assembly thereon, and rotatable between a first orientation and a second orientation to thereby articulate the end effector assembly between an aligned position and an articulated position. A spring is operably associated with the articulation block and configured to bias the articulation block towards the second orientation. In response to actuation of the actuator, the inner shaft is moved from an un-actuated position to an actuated position to move the articulation block from a proximal position, wherein the end effector assembly is disposed in a retracted position within the outer shaft thereby retaining the articulation block in the first orientation against the bias of the spring, to a distal position, wherein the end effector assembly extends distally from the outer shaft to permit the articulation block to rotate to the second orientation under the bias of the spring to thereby articulate the end effector assembly from the aligned position to the articulated position.

In an aspect of the present disclosure, the articulation block is pivotable relative to the inner shaft about a pivot pin. In such aspects, the spring may be a torsion spring disposed about the pivot pin.

In another aspect of the present disclosure, the end effector assembly includes first and second arms configured to support a tissue specimen bag thereon. In aspects, an operable dimension of the first and second arms of the end effector assembly inhibit articulation of the end effector assembly within the outer shaft in the retracted position.

In still another aspect of the present disclosure, the actuator is slidable relative to the housing between the un-actuated position and the actuated position.

Another tissue specimen retrieval device provided in accordance with aspects of the present disclosure includes a housing, an outer shaft extending distally from the housing and defining a longitudinal axis, an end effector assembly extending distally from the outer shaft in a deployed position of the end effector assembly, an actuator operably associated with the housing, and an articulation mechanism operably coupled between the actuator and the end effector assembly. The articulation mechanism includes an articulation block supporting the end effector assembly thereon and rotatable about a pivot. First and second actuation bars are coupled to the articulation block on respective first and second sides of the pivot at respective distal end portions thereof and to the actuator at respective proximal end portions thereof. Actuation of the actuator from an un-actuated position to a first actuated position moves the first actuation bar in a proximal direction and the second actuation bar in a distal direction to thereby rotate the articulation block such that the end effector assembly is articulated in a first direction from an aligned position to a first articulated position. Actuation of the actuator from the un-actuated position to a second actuated position moves the first actuation bar in the distal direction and the second actuation bar in the proximal direction to thereby rotate the articulation block such that the end effector assembly is articulated in a second, opposite direction from the aligned position to a second articulated position.

In an aspect of the present disclosure, the actuator is actuated in one direction from the un-actuated position to the first actuated position and in an opposite direction from the un-actuated position to the second actuated position.

In another aspect of the present disclosure, the actuator is movable about a second pivot between the un-actuated position and the first and second actuated positions, and the first actuation bar is coupled to the actuator on a first side of the second pivot with the second actuation bar coupled to the actuator on a second, opposite side of the second pivot.

In yet another aspect of the present disclosure, the end effector assembly includes first and second arms configured to support a tissue specimen bag thereon.

In still another aspect of the present disclosure, the end effector assembly is deployable relative to the outer shaft from a retracted position, wherein the end effector assembly is disposed within the outer shaft, to the deployed position.

In still yet another aspect of the present disclosure, another actuator is operably associated with the housing and configured to selectively deploy the end effector assembly from the retracted position to the extended position.

In another aspect of the present disclosure, the actuator is translatable to deploy the end effector assembly and rotatable to articulate the end effector assembly.

BRIEF DESCRIPTION OF THE DRAWINGS

The above and other aspects and features of the present disclosure will become more apparent in view of the following detailed description when taken in conjunction with the accompanying drawings wherein like reference numerals identify similar or identical elements.

DETAILED DESCRIPTION

The present disclosure provides articulation mechanisms for tissue specimen retrieval devices and tissue specimen retrieval devices incorporating the same to facilitate retrieval of tissue from the internal body cavity.

Turning to FIGS. 1-4 A-D, a tissue specimen retrieval device provided in accordance with the present disclosure is shown generally identified by reference numeral 100. Tissue specimen retrieval device 100 includes a housing 110, first and second actuators 120, 130 operably associated with housing 110, an outer shaft 140 extending distally from housing 110, an end effector assembly 150 selectively deployable from the distal end of outer shaft 140, and an articulation mechanism 180 configured to enable selective articulation of end effector assembly 150 relative to outer shaft 140 in the deployed position of end effector assembly 150.

Housing 110, although illustrated as defining a generally tubular configuration, may define any suitable configuration to facilitate grasping and manipulating tissue specimen retrieval device 100 such as, for example, a pencil-grip configuration, a pistol-grip configuration, etc., and may include any suitable features to enhance ergonomics such as, for example, recesses, protrusions, textured surfaces, finger rings, etc.

First actuator 120 is operably associated with housing 110 and coupled to outer shaft 140 to enable selective extension and retraction of outer shaft 140 relative to housing 110 and, thus, end effector assembly 150, to selectively move end effector assembly 150 between a retracted position (FIG. 1) and a deployed position (FIG. 2) relative to outer shaft 140 in response to actuation of first actuator 120. Alternatively, first actuator 120 may be coupled to end effector assembly 150 to enable selective extension and retraction of end effector assembly 150 relative to housing 110 and, thus, outer shaft 140, to similarly move end effector assembly 150 between a retracted position (FIG. 1) and a deployed position (FIG. 2) relative to outer shaft 140. First actuator 120 may be configured as a sliding actuator slidable along housing 110, as illustrated, or may define any other suitable configuration such as, for example, a plunger actuator that is selectively manipulatable relative to housing 110 along a longitudinal axis of housing 110, a pivoting actuator pivotable relative to housing 110, etc.

Second actuator 130 is operably associated with housing 110 and coupled to articulation mechanism 180 (FIGS. 4A-4D) to enable selective articulation of end effector assembly 150 relative to outer shaft 140, once deployed from outer shaft 140, between an aligned position (FIG. 2) and an articulated position (FIG. 3), in response to actuation of second actuator 130. Second actuator 130 may be configured as a plunger actuator that is selectively manipulatable relative to housing 110 along a longitudinal axis of housing 110, as illustrated, or may define any other suitable configuration such as, for example, a pivoting actuator pivotable relative to housing 110, a sliding actuator slidable along housing 110, etc.

Figure 1:
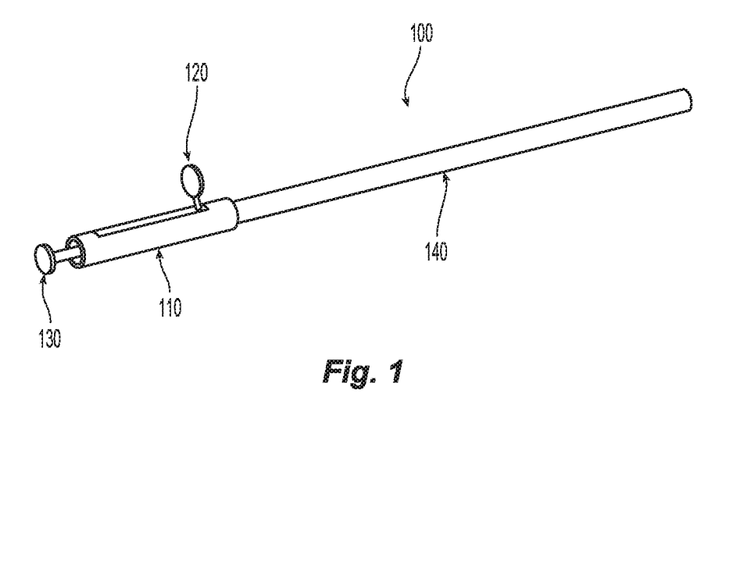
FIG. 1 is a side, perspective view of a tissue specimen retrieval device provided in accordance with aspects of the present disclosure, wherein an end effector assembly of the tissue specimen retrieval device is disposed in a retracted position.
Figure 2:
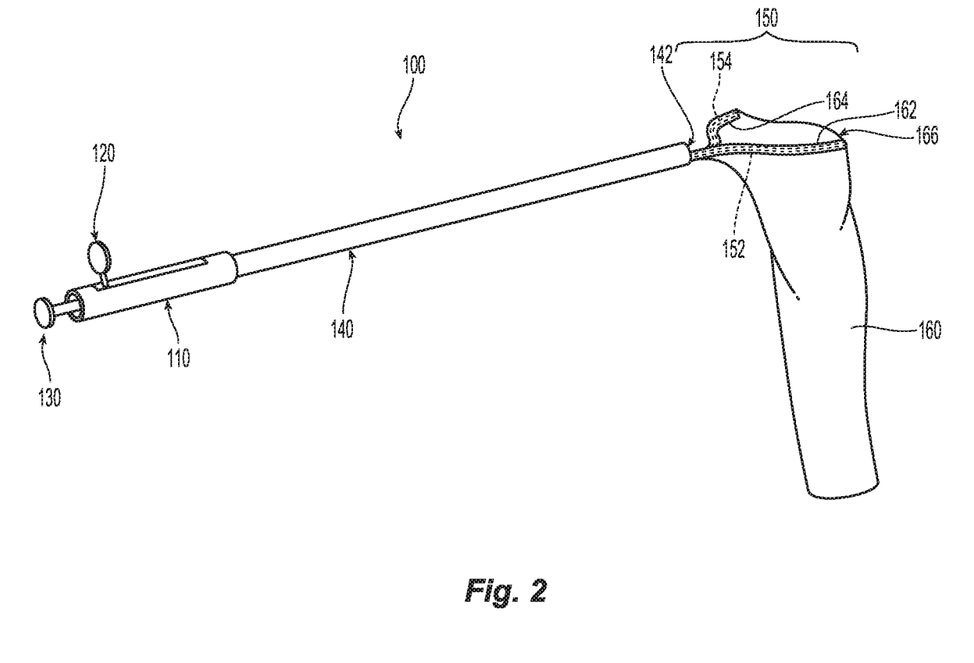
FIG. 2 is a side, perspective view of the tissue specimen retrieval device of FIG. 1, wherein the end effector assembly is disposed in a deployed, aligned position.
Figure 7:
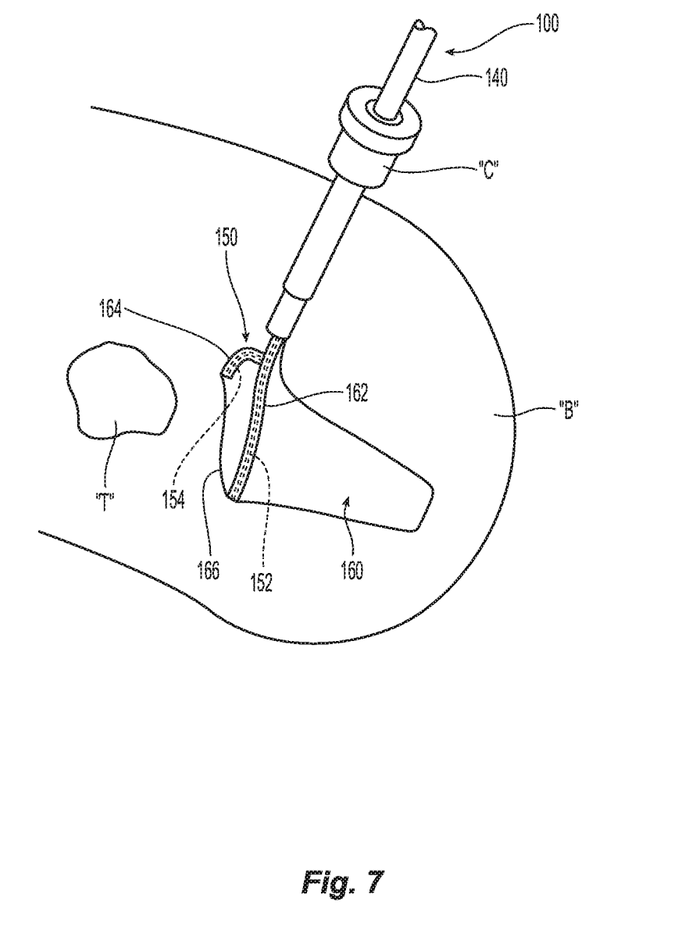
FIG. 7 is a perspective view of the tissue specimen retrieval device of FIG. 1 inserted through an access cannula into an internal body cavity for retrieval of a tissue specimen therefrom.

Continuing with reference to FIGS. 1-4 A-D, outer shaft 140 extends distally from housing 110, as noted above, and is configured for insertion through an access cannula "C" (FIG. 7) or natural passageway into an internal body cavity "B" (FIG. 7). Outer shaft 140 may be substantially rigid (within manufacturing tolerances and in response to reasonable loads applied thereto) or may include one or more portions configured to flex and/or articulate relative to a longitudinal axis thereof. A lumen 142 extends longitudinally through outer shaft 140. Outer shaft 140, as noted above, is slidable relative to housing 110 and end effector assembly 150 to enable selective deployment of end effector assembly 150 from outer shaft 140. More specifically, outer shaft 140 is movable between a distal position, corresponding to the retracted position of end effector assembly 150 (see FIG. 1), wherein end effector assembly 150 is disposed within lumen 142 of outer shaft 140, and a proximal position, corresponding to the deployed position of end effector assembly 150 (FIG. 2), wherein end effector assembly 150 extends distally from outer shaft 140. As an alternative to outer shaft 140 moving relative to housing 110 to deploy end effector assembly 150, as also noted above, end effector assembly 150 may be selectively movable relative to housing 110 and outer shaft 140 to enable deployment of end effector assembly 150 from outer shaft 140 from the retracted position (FIG. 1) to the deployed position (FIG. 2).

End effector assembly 150 includes a pair of arms 152, 154 and a tissue specimen bag 160 depending from arms 152, 154. Arms 152, 154 are configured for positioning within one or more channels 152, 154 formed about at least a portion of open end 166 of tissue specimen bag 160 to retain tissue specimen bag 160 on arms 152, 154. In the retracted position of end effector assembly 150, arms 152, 154 may be resiliently flexed inwardly to enable accommodation of arms 152, 154 within lumen 142 of outer shaft 140. Tissue specimen bag 160 may be furled, folded, or otherwise positioned in the retracted position of end effector assembly 150 to enable accommodation of tissue specimen bag 160 within lumen 142 of outer shaft 140. Upon deployment of end effector assembly 150 form outer shaft 140, arms 152, 154 are configured to resiliently return to a spaced-apart, curved configuration for retaining tissue specimen bag 160 thereon in an open condition, thus enabling insertion of a tissue specimen "T" (FIG. 7) through open end 166 of tissue specimen bag 160 and into the interior thereof. The resilient return of arms 152, 154 may also serve to unfold, unfurl, or otherwise manipulate tissue specimen bag 160 upon deployment from outer shaft 140.

Tissue specimen bag 160 may be formed from any suitable bio-compatible material (or materials), e.g., ripstop nylon, configured to retain a tissue specimen "T" (FIG. 7) therein. As noted above, tissue specimen bag 160 depends from arms 152, 154 in the deployed position of end effector assembly 150 such that articulation of arms 152, 154 likewise articulates tissue specimen bag 160. Tissue specimen bag 160 defines at least one opening, e.g., at open end 166 thereof, and includes one or more channels 162, 164 formed about open end 166 thereof for receipt of arms 152 154, respectively, therein. The one or more channels 162, 164 may be separate or in communication with one another, and/or may extend about only a portion of open end 166 of tissue specimen bag 160 or about the entirety perimeter thereof. One or more of the openings of tissue specimen bag 160, e.g., open end 166, may include a cinch cord (not shown) disposed thereabout to enable selective closure of the opening. Tissue specimen bag 160 may be disengaged from arms 152, 154 upon cinching closed open end 166 of tissue specimen bag 160, retraction of end effector assembly 150 back towards the retracted position (FIG. 1), using a separate instrument, e.g., grasping device, and/or in any other suitable manner.

With reference to FIGS. 4A-4D, an inner shaft 170 extends through outer shaft 140 and pivotably supports end effector assembly 150 at a distal end portion of inner shaft 170 via a pivot pin 172 and an articulation block 182 of articulation mechanism 180. In embodiments, such as the illustrative embodiment, where end effector assembly 150 is longitudinally fixed relative to housing 110 and outer shaft 140 is movable relative to end effector assembly 150 and housing 110 to deploy end effector assembly 150, inner shaft 170 is longitudinally fixed to housing 110 at a proximal end portion of inner shaft 170. In embodiments, on the other hand, where outer shaft 140 is longitudinally fixed relative to housing 110 and end effector assembly 150 is movable relative to outer shaft 140 and housing 110 to deploy end effector assembly 150, inner shaft 170 is operably coupled to first actuator 120 at a proximal end portion of inner shaft 170 to enable movement of inner shaft 170 relative to housing 110 in response to actuation of first actuator 120.

In embodiments, a rotation knob (not shown) associated with housing 110 and operably coupled to end effector assembly 150, e.g., via inner shaft 170, may be provided to enable selective rotation of end effector assembly 150 about the longitudinal axis of outer shaft 140 and relative to housing 110.

Figure 3:
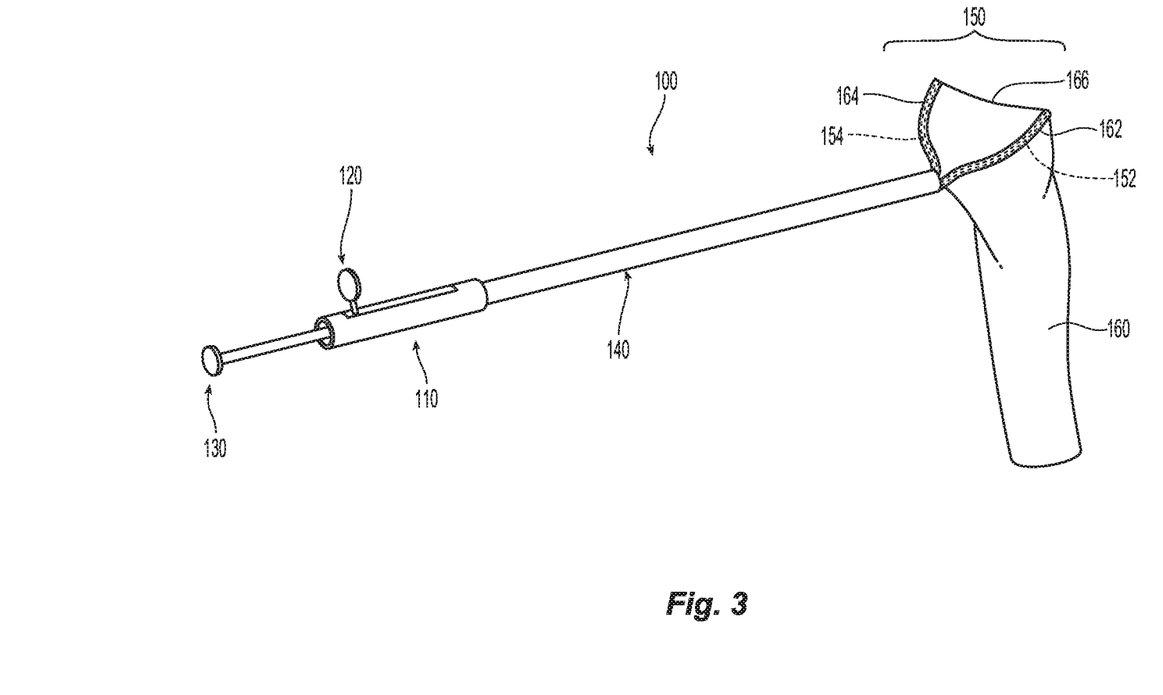
FIG. 3 is a side, perspective view of the tissue specimen retrieval device of FIG. 1, wherein the end effector assembly is disposed in a deployed, articulated position.

Referring to FIGS. 4A-4D, articulation mechanism 180 operably couples second actuator 130 with arms 152, 154 of end effector assembly 150 to enable selective articulation of end effector assembly 150 (and, thus, tissue specimen bag 160 (FIGS. 2 and 3)) relative to outer shaft 140 when end effector assembly 150 is disposed in the deployed position (FIGS. 2 and 3). Articulation mechanism 180 includes an articulation block 182, a torsion spring 184, and an actuation sleeve 186 that is slidably disposed within outer shaft 140 and about inner shaft 170.

Articulation block 182 is pivotably coupled to inner shaft 170 via pivot pin 172 and supports proximal ends of arms 152, 154 of end effector assembly 150 thereon such that rotation of articulation block 182 about pivot pin 172 articulates arms 152, 154 relative to outer shaft 140. Articulation block 182 defines a generally rectangular configuration having a length greater than a diameter of actuation sleeve 186 and a width less than the diameter of actuation sleeve 186 such that, in a first orientation, wherein the length of articulation block 182 is sufficiently aligned on the longitudinal axis of outer shaft 140, articulation block 182 is capable of being received within actuation sleeve 186 and such that, in at least one second orientation, wherein the length of articulation block 182 is sufficiently angled relative to actuation sleeve 186, articulation block 182 is inhibited from being received within actuation sleeve 186. In embodiments, in one second orientation, the width of articulation block 182 is aligned on the longitudinal axis of outer shaft 140 such that articulation block 182 rotates 90 degrees between the first and second orientations, although additional or alternative second orientation angles, e.g., 45 degrees, 60 degrees, etc., are also contemplated. In order to accommodate one or more second orientation positions, in embodiments, articulation block 182 may define any other suitable shape having at least two dimensions wherein one of the dimensions is greater than the diameter of actuation sleeve 186 and the other of the dimensions is less than the diameter of actuation sleeve 186.

Torsion spring 184 is disposed about pivot pin 172 and coupled to articulation block 182 to bias articulation block 182 towards the second orientation, wherein the width of articulation block 182 inhibits the return of articulation block 182 into actuation sleeve 186. Articulation block 182 is initially disposed within actuation sleeve 186 such that articulation block 182 is maintained in the first orientation against the bias of torsion spring 184.

Actuation sleeve 186, as mentioned above, is slidably disposed within outer shaft 140 and about inner shaft 170. Actuation sleeve 186 is coupled to second actuator 130 at a proximal end portion of actuation sleeve 186 such that actuation of second actuator 130 translates actuation sleeve 186 between an engaged position (FIG. 4B), wherein actuation sleeve 186 is disposed at least partially about articulation block 182 to maintain articulation block 182 in the first orientation against the bias of torsion spring 184, and a disengaged position (FIG. 4C), wherein actuation sleeve 186 is proximally-spaced from articulation block 182 to enable articulation block 182 to rotate to the at least one second orientation under the bias of torsion spring 184. Actuation sleeve 186 may further be moved from the disengaged position (FIG. 4C) to a locked position (FIG. 4D), wherein actuation sleeve 186 abuts articulation block 182, thereby locking articulation block 182 in one of the second orientations by inhibiting return thereof towards the first orientation. The second orientation corresponding to the disengaged position (FIG. 4C) may be the same as the second orientation corresponding to the locked position (FIG. 4D), e.g., both 90 degrees from the first orientation, or may be different, wherein, upon movement to the locked position, actuation sleeve 186 urges articulation block 182 to rotate further before abutting articulation block 182 in the locked position (FIG. 4D) such that the second orientation corresponding to the disengaged position (FIG. 4C) is different from the second orientation corresponding to the locked position (FIG. 4D), e.g., 45 degrees and 90 degrees, respectively, from the first orientation.

Figure 4A:
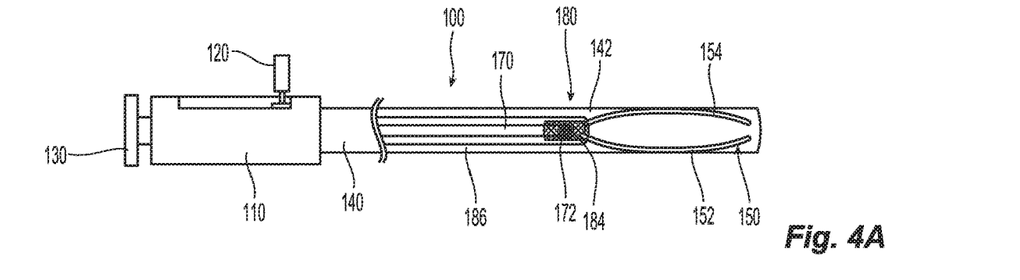
FIG. 4A is a side, partial cross-sectional view of the tissue specimen retrieval device of FIG. 1, with the specimen bag removed, and the end effector assembly disposed in the retracted position.

With reference to FIGS. 1-4D and 7, and initially to FIGS. 1 and 4A, in use, end effector assembly 150 is initially disposed in the retracted position to facilitate insertion of tissue specimen retrieval device 100 through an access cannula "C" (FIG. 7) or natural passageway into an internal body cavity "B" (FIG. 7). Further, actuation sleeve 186 is initially disposed in the engaged position, wherein actuation sleeve 186 is disposed at least partially about articulation block 182 to maintain articulation block 182 in the first orientation against the bias of torsion spring 184.

Figure 4B:
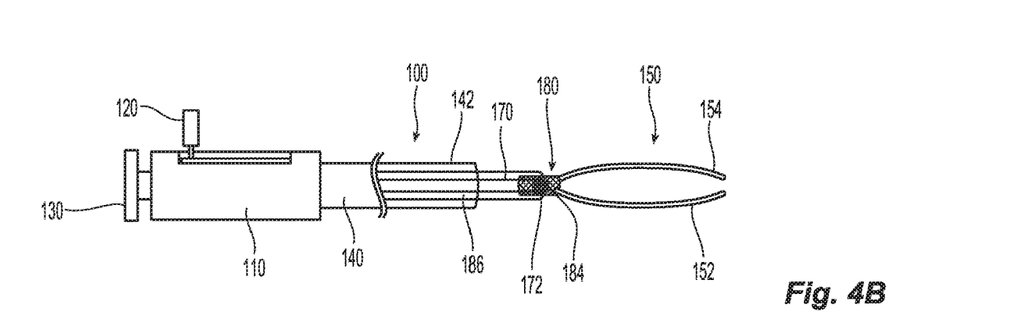
FIG. 4B is a side, partial cross-sectional view of the tissue specimen retrieval device of FIG. 1, with the specimen bag removed, and the end effector assembly disposed in the deployed, aligned position.

Once tissue specimen retrieval device 100 is disposed within the internal body cavity "B" (FIG. 7) as desired, and with reference to FIGS. 2 and 4B, end effector assembly 150 is deployed from outer shaft 140 by actuating first actuator 120 from a more-distal position to a more-proximal position to thereby withdraw outer shaft 140 proximally from about end effector assembly 150 such that end effector assembly 150 is deployed to the deployed position. At this point, end effector assembly 150 remains aligned on the longitudinal axis of outer shaft 140 and actuation sleeve 186 remains disposed in the engaged position.

Figure 4C:
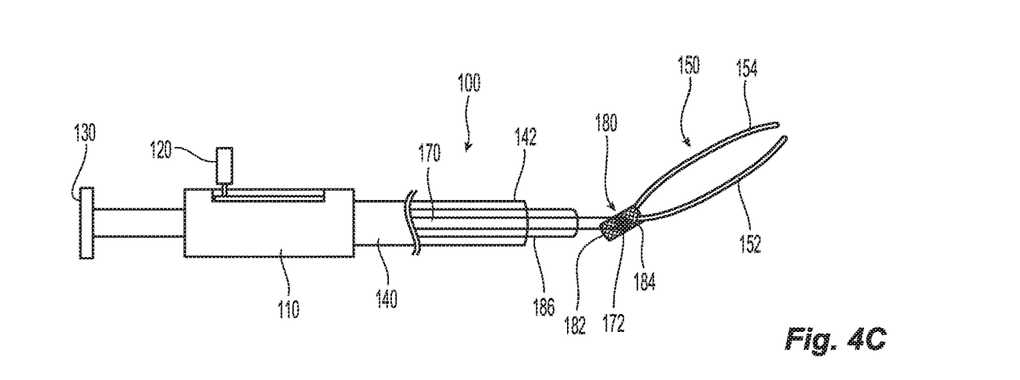
FIG. 4C is a side, partial cross-sectional view of the tissue specimen retrieval device of FIG. 1, with the specimen bag removed, and the end effector assembly disposed in the deployed, articulated position.

Referring to FIG. 4C, if it is desired to articulate end effector assembly 150 relative to outer shaft 140 after end effector assembly 150 is deployed from outer shaft 140, second actuator 130 is moved proximally from a closer position relative to housing 110 to a further proximally-spaced position relative to housing 110 to thereby slide actuation sleeve 186 proximally about and relative to end effector assembly 150 and articulation block 182 from the engaged position (FIG. 4B) to the disengaged position (FIG. 4C), such that actuation sleeve 186 is proximally-spaced from articulation block 182 to enable articulation block 182 to rotate to the second orientation under the bias of torsion spring 184, thereby articulating end effector assembly 150 relative to outer shaft 140. More specifically, articulation block 182, once no longer constrained by actuation sleeve 186, may be configured to move, under the bias of torsion spring 184, to any suitable articulated position relative to outer shaft 140 such as, for example, a 45 degree articulated position, 60 degree articulated position, or a 90 degree articulated position, to similarly articulate end effector assembly 150 relative to outer shaft 140. With actuation sleeve 186 disposed in the disengaged position (FIG. 4C), end effector assembly 150 is disposed in an articulated position relative to outer shaft 140 but may be urged back towards alignment with the longitudinal axis of outer shaft 140 or may be articulated further off of the longitudinal axis of outer shaft 140, e.g., in response to sufficient force on end effector assembly 150 to overcome the biasing force of torsion spring 184.

Figure 4D:
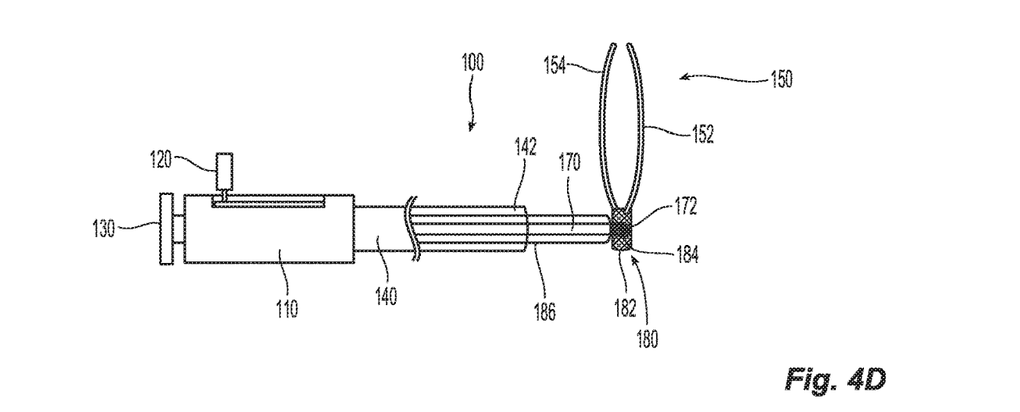
FIG. 4D is a side, partial cross-sectional view of the tissue specimen retrieval device of FIG. 1, with the specimen bag removed, and the end effector assembly disposed in a deployed, further articulated, locked position.

With reference to FIG. 4D, in order to lock end effector assembly 150 in an articulated position, e.g., the same or a different second orientation as end effector assembly 150 is positioned under the bias of torsion spring 184, second actuator 130 is returned proximally towards the closer position relative to housing 110 to thereby return actuation sleeve 186 distally relative to articulation block 182. However, instead of receiving articulation block 182 therein, actuation sleeve 186 is moved to a locked position wherein actuation sleeve 186 abuts articulation block 182. As noted above, actuation sleeve 186 may abut articulation block 182 to maintain articulation block 182 in the same second orientation, or may further urge articulation block 182 to rotate before locking articulation block 182 in a further articulated second orientation. In either configuration, locking is achieved because, with articulation block 182 disposed in one of the second orientations, articulation block 182 is inhibited from passing into actuation sleeve 186. Rather, actuation sleeve 186 abuts articulation block 182 on either side of pivot pin 172 to inhibit pivoting of articulation block 182 from the second orientation, thereby locking end effector assembly 150 in the articulated position.

Turning momentarily to FIG. 7, the above-detailed articulation of end effector assembly 150 of tissue specimen retrieval device 100 facilitates orientation of open end 166 of tissue specimen bag 160 in an appropriate position within the internal body cavity "B" to facilitate positioning of a tissue specimen "T" therein.

End effector assembly 150 may be returned to the retracted position, which also serves to return end effector assembly 150 to the aligned position, by actuating first actuator 120 from the more-proximal position to the more-distal position to advance outer shaft 140 about end effector assembly 150. As such, end effector assembly 150 is moved to the aligned position and returned to the retracted position to facilitate retrieval of end effector assembly 150 from the internal body cavity "B."

Figure 5A:
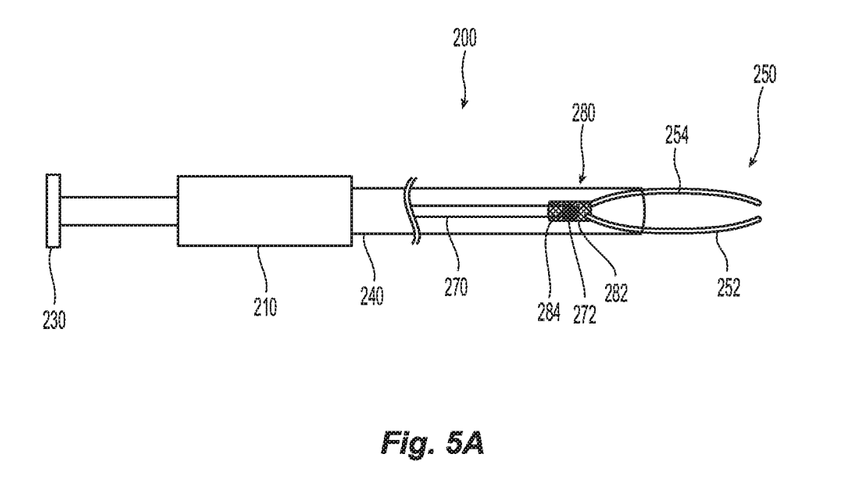
FIG. 5A is a side, partial cross-sectional view of another tissue specimen retrieval device provided in accordance with aspects of the present disclosure, with the specimen bag removed, and the end effector assembly disposed in a partially-deployed, aligned position.
Figure 5B:
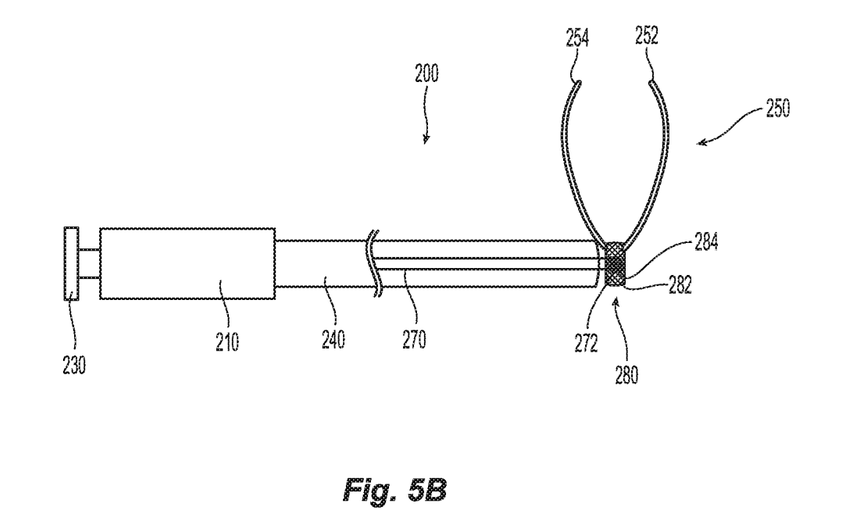
FIG. 5B is a side, partial cross-sectional view of the tissue specimen retrieval device of FIG. 6A, with the specimen bag removed, and the end effector assembly disposed in a deployed, articulated position.

Referring to FIGS. 5A and 5B, another tissue specimen retrieval device provided in accordance with the present disclosure is shown generally identified by reference numeral 200. Tissue specimen retrieval device 200 includes a housing 210, an actuator 230 operably associated with housing 210, an outer shaft 240 extending distally from housing 210, an end effector assembly 250 selectively deployable from the distal end of outer shaft 240, and an articulation mechanism 280 configured to enable selective articulation of end effector assembly 250 relative to outer shaft 240. Tissue specimen retrieval device 200 is similar to tissue specimen retrieval device 100 (FIGS. 1-4D and 7) and may include any of the features thereof, except as specifically contradicted below.

Actuator 230 of tissue specimen retrieval device 200 is operably associated with housing 210 and coupled to articulation mechanism 280 to enable both selective movement of end effector assembly 250 between a retracted position and a deployed position (FIG. 5B) relative to outer shaft 240, and to articulate end effector assembly 250 relative to outer shaft 240 upon deployment of end effector assembly 250 from outer shaft 240. Actuator 230 may be configured as a plunger actuator that is selectively manipulatable relative to housing 210 along a longitudinal axis of housing 210, as illustrated, or may define any other suitable configuration.

Outer shaft 240 is fixed relative to and extends distally from housing 210, while an inner shaft 270 extends through outer shaft 240 and pivotably supports end effector assembly 250 at a distal end portion of inner shaft 270 via a pivot pin 272 and an articulation block 282 of articulation mechanism 280. Inner shaft 270 is operably coupled to actuator 230 at a proximal end portion of inner shaft 270 to enable movement of inner shaft 270 relative to housing 210 and through outer shaft 240 in response to actuation of actuator 230. More specifically, movement of actuator 230 distally from a further proximally-spaced position relative to housing 110 to a closer position relative to housing 110 moves inner shaft 270 distally through outer shaft 240 to move end effector assembly 250 to the deployed position, wherein end effector assembly 250 extends distally from outer shaft 240.

Articulation mechanism 280 operably couples actuator 230 with arms 252, 254 of end effector assembly 250 and includes an articulation block 282 and a torsion spring 284. Articulation block 282 is pivotably coupled to inner shaft 270 via pivot pin 272 and supports proximal ends of arms 252, 254 of end effector assembly 250 thereon such that rotation of articulation block 282 about pivot pin 272 articulates arms 252, 254 relative to outer shaft 240. Articulation block 282 is rotatable about pivot pin 272 between a first orientation, corresponding to an aligned position of end effector assembly 250 relative to a longitudinal axis of outer shaft 240, and a second orientation, corresponding to an articulated position of end effector assembly 250 relative to the longitudinal axis of outer shaft 240. In embodiments, articulation block 282 rotates 90 degrees between the first and second orientations, although other suitable rotation angles, e.g., 45 degrees, 60 degrees, etc., are also contemplated.

Torsion spring 284 is disposed about pivot pin 272 and coupled to articulation block 282 to bias articulation block 282 towards the second orientation. Prior to deployment of end effector assembly 250, articulation block 282 is disposed within outer shaft 240, wherein arms 252, 254 of end effector assembly 250 are constrained in a substantially aligned position relative to the longitudinal axis of outer shaft 240 via outer shaft 240, thereby maintaining articulation block 282 in the first orientation against the bias of torsion spring 284.

Continuing with reference to FIGS. 5A and 5B, in use, end effector assembly 250 is initially disposed in the retracted position to facilitate insertion of tissue specimen retrieval device 200 through an access cannula "C" (FIG. 7) or natural passageway into an internal body cavity "B" (FIG. 7). Once tissue specimen retrieval device 200 is disposed within the internal body cavity "B" (FIG. 7) as desired, end effector assembly 250 is deployed from outer shaft 240 and articulated to the articulated position by actuating actuator 230 distally from the further proximally-spaced position relative to housing 210 to the closer position relative to housing 210. As end effector assembly 250 is no longer constrained by outer tube 240, articulation block 282, under the bias of torsion spring 284, rotates about pivot pin 272 to the second orientation, to similarly articulate end effector assembly 250 relative to outer shaft 240 to any suitable articulated position relative to outer shaft 240 such as, for example, a 90 degree articulated position. In order to return end effector assembly 250 to the retracted position, actuator 230 is returned proximally from the closer position relative to housing 210 to the further proximally-spaced position relative to housing 210.

Figure 6A:
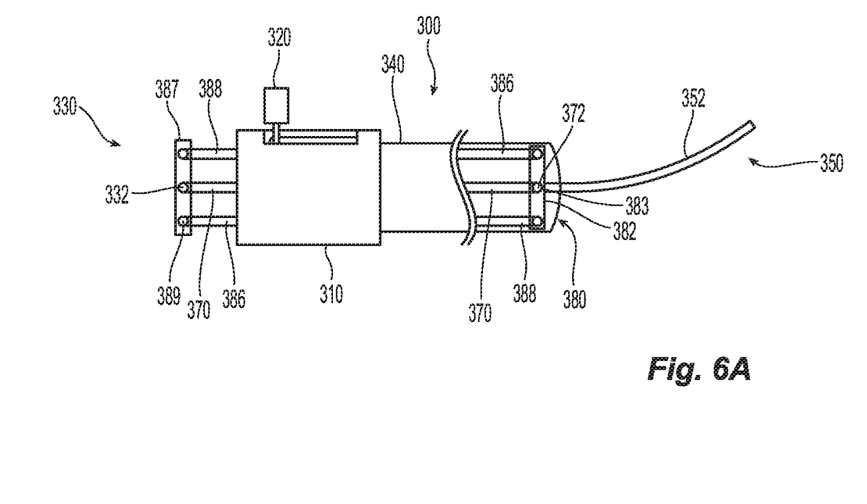
FIG. 6A is a side, partial cross-sectional view of another tissue specimen retrieval device provided in accordance with aspects of the present disclosure, with the specimen bag removed, and the end effector assembly disposed in a deployed, aligned position.
Figure 6B:
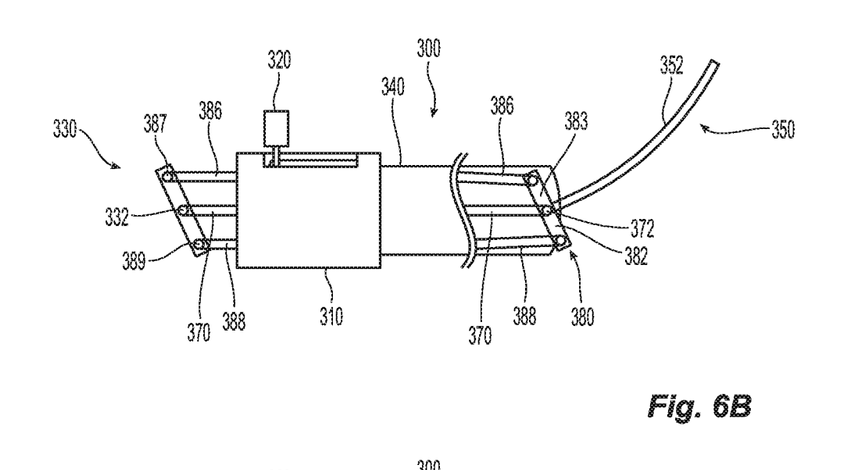
FIG. 6B is a side, partial cross-sectional view of the tissue specimen retrieval device of FIG. 6A, with the specimen bag removed, and the end effector assembly disposed in a deployed, first articulated position.
Figure 6C:
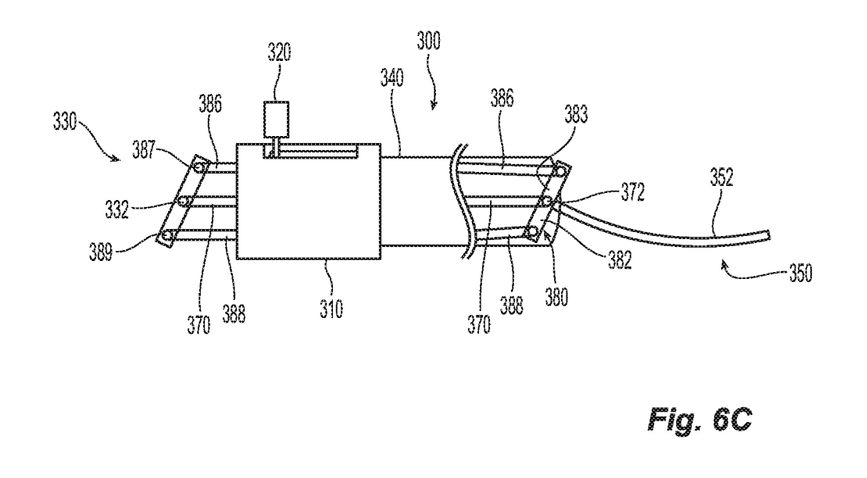
FIG. 6C is a side, partial cross-sectional view of the tissue specimen retrieval device of FIG. 6A, with the specimen bag removed, and the end effector assembly disposed in a deployed, second articulated position.

Turning now to FIGS. 6A-6C, another tissue specimen retrieval device provided in accordance with the present disclosure is shown generally identified by reference numeral 300. Tissue specimen retrieval device 300 includes a housing 310, first and second actuators 320, 330 operably associated with housing 310, an outer shaft 340 extending distally from housing 310, an end effector assembly 350 selectively deployable from the distal end of outer shaft 340, and an articulation mechanism 380 configured to enable selective articulation of end effector assembly 350 relative to outer shaft 340. Tissue specimen retrieval device 300 is similar to tissue specimen retrieval device 100 (FIGS. 1-4D and 7) and may include any of the features thereof, except as specifically contradicted below.

First actuator 320 is operably associated with housing 310 and coupled to outer shaft 340 to enable selective retraction and extension of outer shaft 340 relative to housing 310 and, thus, end effector assembly 350, to selectively move end effector assembly 350 between a retracted position and a deployed position relative to outer shaft 340 in response to actuation of first actuator 320, similarly as detailed above with respect to tissue specimen retrieval device 100 (FIGS. 1-4D and 7).

Second actuator 330 is operably associated with housing 310 and coupled to articulation mechanism 380 to enable selective articulation of end effector assembly 350 relative to outer shaft 340, once deployed from outer shaft 340, between an aligned position (FIG. 6A) and a plurality of articulated positions (FIGS. 6B and 6C), in response to actuation of second actuator 330. Second actuator 330, more specifically, is pivotably coupled to housing 310 about a pivot pin 332 and pivotable relative thereto from a neutral position (FIG. 6A) to a positive pivoted position (FIG. 6B) and a negative pivoted position (FIG. 6C) in order to articulate end effector assembly 350 from an aligned position (FIG. 6A) to a first articulated position (FIG. 6B) and a second articulated position (FIG. 6C), respectively. Second actuator 330 may be configured as a tilting actuator, as illustrated, or may be configured as rotation knob rotatable about pivot pin 332 (wherein the positive and negative positions are rotational positions in opposite directions from a neutral position of the rotation knob).

An inner shaft 370 extends through outer shaft 340 and pivotably supports end effector assembly 350 at a distal end portion of inner shaft 370 via a pivot pin 372 and an articulation block 382 of articulation mechanism 380. Inner shaft 370 is fixed relative to housing 310 and outer shaft 340 is movable relative thereto to deploy and retract end effector assembly 350 or, in other embodiments, outer shaft 340 is fixed relative to housing 310 and inner shaft 370 is movable relative thereto to deploy and retract end effector assembly 350. In embodiments where inner shaft 370 is movable, first actuator 320 may be eliminated and inner shaft 370 couples second actuator 330 with second actuator 330 also being longitudinally movable relative to housing 310. In such embodiments, longitudinal movement of second actuator 330 relative to housing 310 moves inner shaft 370 through outer shaft 340 to deploy and retract end effector assembly 350, while pivoting of second actuator 330 relative to housing 310, as noted above, articulates end effector assembly 350 relative to housing 310.

Continuing with reference to FIGS. 6A-6C, articulation mechanism 380 operably couples second actuator 330 with arms 352 of end effector assembly 350 to enable selective articulation of end effector assembly 350 relative to outer shaft 340 when end effector assembly 350 is disposed in the deployed position. Articulation mechanism 380 includes an articulation block 382, a first actuation bar 386, and a second actuation bar 388.

Articulation block 382 is pivotably coupled to inner shaft 370 via pivot pin 372 extending through a central portion 383 of articulation block 382 and supports proximal ends of arms 352 of end effector assembly 350 thereon such that rotation of articulation block 382 about pivot pin 372 articulates arms 352 relative to outer shaft 340. First actuation bar 386 is pivotably coupled at a distal end portion thereof to articulation block 382 on one side of central portion 383 (and, thus, on one side of pivot pin 372), while second actuation bar 388 is pivotably coupled at a distal end portion thereof to articulation block 382 on the other side of central portion 383 (and, thus, on the other side of pivot pin 372). The proximal end portions of first and second actuation bars 386, 388, respectively, are coupled to second actuator 330 via pin and slot engagements 387, 389, respectively, on opposing sides of pivot pin 332.

As a result of the above-detailed configuration, pivoting of second actuator 330 relative to housing 310 from the neutral position (FIG. 6A) to the positive pivoted position (FIG. 6B) pulls first actuation bar 386 proximally and pushes second actuation bar 388 distally, thereby urging articulation block 382 to rotate in a first direction, e.g., counter-clockwise from the orientation illustrated in FIGS. 6A-6C, thus articulating end effector assembly 350 in a first direction off of the longitudinal axis of outer shaft 340. On the other hand, pivoting of second actuator 330 relative to housing 310 from the neutral position (FIG. 6A) to the negative pivoted position (FIG. 6C) pushes first actuation bar 386 distally and pulls second actuation bar 388 proximally, thereby urging articulation block 382 to rotate in a second, opposite direction, e.g., clockwise from the orientation illustrated in FIGS. 6A-6C, thus articulating end effector assembly 350 in a second, opposite direction off of the longitudinal axis of outer shaft 340.

In use, end effector assembly 350 is initially disposed in the retracted position to facilitate insertion of tissue specimen retrieval device 300 through an access cannula "C" (FIG. 7) or natural passageway into an internal body cavity "B" (FIG. 7). Once tissue specimen retrieval device 300 is disposed within the internal body cavity "B" (FIG. 7) as desired, end effector assembly 350 is deployed from outer shaft 340 and articulated to a desired position by actuating first actuator 320 and second actuator 330, respectively. In order to return end effector assembly 350 to the retracted position, first actuator 320 is returned to its initial position.

From the foregoing and with reference to the various drawings, those skilled in the art will appreciate that certain modifications can be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A tissue specimen retrieval device, comprising:
a housing;
an end effector assembly distally-spaced from the housing;
an actuator operably associated with the housing; and
an articulation mechanism operably coupled between the actuator and the end effector assembly, the articulation mechanism including:
an articulation block supporting the end effector assembly thereon, the articulation block rotatable between a first orientation, a second orientation, and a third orientation to thereby articulate the end effector assembly between an aligned position and an articulated position;
a spring operably associated with the articulation block and configured to bias the articulation block towards the second orientation; and
an actuation sleeve defining a distal end portion, wherein, in response to actuation of the actuator, relative sliding between the actuation sleeve and the articulation block is effected from an engaged position, wherein the actuation sleeve is disposed about at least a portion of the articulation block to thereby retain the articulation block in the first orientation, to a disengaged position, wherein the actuation sleeve is positioned proximally of the articulation block such that the articulation block rotates to the second orientation under the bias of the spring, and wherein distally advancing the actuation sleeve such that the distal end portion of the actuation sleeve pushes against the articulation block rotates the articulation block from the second orientation to the third orientation to thereby articulate the end effector assembly to the articulated position.

2. The tissue specimen retrieval device according to claim 1, wherein, in the first orientation, the articulation block defines a first operable dimension less than a diameter of the actuation sleeve to permit receipt of the articulation block within the actuation sleeve, and wherein, in the second orientation, the articulation block defines a second operable dimension greater than the diameter of the actuation sleeve to inhibit return of the articulation block into the actuation sleeve.

3. The tissue specimen retrieval device according to claim 1, wherein the articulation block is pivotable about a pivot pin and wherein the spring is a torsion spring disposed about the pivot pin.

4. The tissue specimen retrieval device according to claim 1, further comprising an outer shaft, wherein the end effector assembly is deployable relative to the outer shaft from a retracted position, wherein the end effector assembly is disposed within the outer shaft, to a deployed position, wherein the end effector assembly extends from the outer shaft.

5. The tissue specimen retrieval device according to claim 4, further comprising another actuator operably associated with the housing and configured to selectively deploy the end effector assembly from the retracted position to the deployed position.

6. The tissue specimen retrieval device according to claim 4, wherein deployment of the end effector assembly relative to the outer shaft includes sliding the end effector assembly distally relative to the outer shaft and the housing.

7. The tissue specimen retrieval device according to claim 1, wherein relative sliding between the actuation sleeve and the articulation block from the engaged position to the disengaged position includes sliding the actuation sleeve proximally relative to the articulation block.

8. A tissue specimen retrieval device, comprising:
a housing;
an outer shaft extending distally from the housing and defining a longitudinal axis;
an end effector assembly distally-spaced from the housing, the end effector assembly slidable relative to the outer shaft from a retracted position, wherein the end effector assembly is disposed within the outer shaft, to a deployed position, wherein the end effector assembly extends from the outer shaft;
a first actuator operably associated with the housing and coupled to the end effector assembly for sliding the end effector assembly between the retracted and deployed positions;
a second actuator operably associated with the housing; and
an articulation mechanism operably coupled between the second actuator and the end effector assembly, the articulation mechanism including:
an articulation block supporting the end effector assembly thereon, the articulation block rotatable between a first orientation, a second orientation, and a third orientation to thereby articulate the end effector assembly between an aligned position and an articulated position;
a spring operably associated with the articulation block and configured to bias the articulation block towards the second orientation; and
an actuation sleeve defining a distal end portion, the actuation sleeve slidable relative to the articulation block, in response to actuation of the second actuator, from an engaged position, wherein the actuation sleeve is disposed about at least a portion of the articulation block to thereby retain the articulation block in the first orientation, to a disengaged position, wherein the actuation sleeve is positioned proximally of the articulation block such that the articulation block rotates to the second orientation under the bias of the spring, and wherein distally advancing the actuation sleeve such that the distal end portion of the actuation sleeve pushes against the articulation block rotates the articulation block from the second orientation to the third orientation to thereby articulate the end effector assembly to the articulated position.

9. The tissue specimen retrieval device according to claim 8, wherein, in the first orientation, the articulation block defines a first operable dimension less than a diameter of the actuation sleeve to permit receipt of the articulation block within the actuation sleeve, and wherein, in the second orientation, the articulation block defines a second operable dimension greater than the diameter of the actuation sleeve to inhibit return of the articulation block into the actuation sleeve.

10. The tissue specimen retrieval device according to claim 8, wherein the articulation block is pivotable about a pivot pin and wherein the spring is a torsion spring disposed about the pivot pin.

* * * * *